United States Patent [19]

Patterson et al.

[11] 4,322,556
[45] * Mar. 30, 1982

[54] METHOD FOR PREPARING ANILINE BY REACTION OF NITROBENZENE AND VINYLCYCLOHEXENE

[75] Inventors: John A. Patterson, Fishkill, N.Y.; Wheeler C. Crawford, Houston; James R. Wilson, Missouri City, both of Tex.

[73] Assignee: Texaco Inc., White Plains, N.Y.

[*] Notice: The portion of the term of this patent subsequent to Nov. 11, 1997, has been disclaimed.

[21] Appl. No.: 191,232

[22] Filed: Sep. 26, 1980

Related U.S. Application Data

[60] Continuation of Ser. No. 16,674, Mar. 1, 1979, abandoned, which is a division of Ser. No. 934,789, Aug. 18, 1978, abandoned.

[51] Int. Cl.$^3$ .................. C07C 85/11; C07C 5/02; C07C 5/42; C07C 5/367
[52] U.S. Cl. .................. 564/423; 564/420; 564/421; 564/422; 585/257; 585/433; 585/434; 585/440; 585/444
[58] Field of Search .............. 564/423, 421, 422, 420

[56] References Cited

U.S. PATENT DOCUMENTS

| B 430,157 | 2/1976 | Juguin et al. | 260/668 D |
| 2,126,817 | 8/1938 | Rosen | 260/683.3 X |
| 2,504,016 | 4/1950 | Foster | 260/666 |
| 2,544,808 | 3/1951 | Stahly | 260/666 |
| 2,971,035 | 2/1961 | Stringer et al. | 260/673.5 |
| 3,156,735 | 11/1964 | Armstrong | 260/680 |
| 3,354,212 | 11/1967 | Donaruma | 260/580 X |
| 3,536,632 | 10/1970 | Kroll | 260/683.3 X |
| 3,674,884 | 7/1972 | Moritani et al. | 260/669 R |
| 4,233,244 | 11/1980 | Patterson et al. | 564/423 |
| 4,237,070 | 12/1980 | Patterson et al. | 564/423 |

FOREIGN PATENT DOCUMENTS

| 45-490 | 1/1970 | Japan | 260/580 |
| 281455 | 12/1970 | U.S.S.R. | 260/580 |

OTHER PUBLICATIONS

Kozlov et al., "Chem. Ab., " vol. 65, Ab. No. 18451g, (1966).

*Primary Examiner*—John Doll
*Attorney, Agent, or Firm*—Carl G. Ries; Robert A. Kulason; Carl G. Seutter

[57] ABSTRACT

Aniline may be prepared by reaction of nitrobenzene and vinylcyclohexene at 170° C.–300° C., typically 200° C., in the presence of a homogeneous catalyst typified by $IrCl(CO)(Ph_3P)_2$.

26 Claims, 1 Drawing Figure

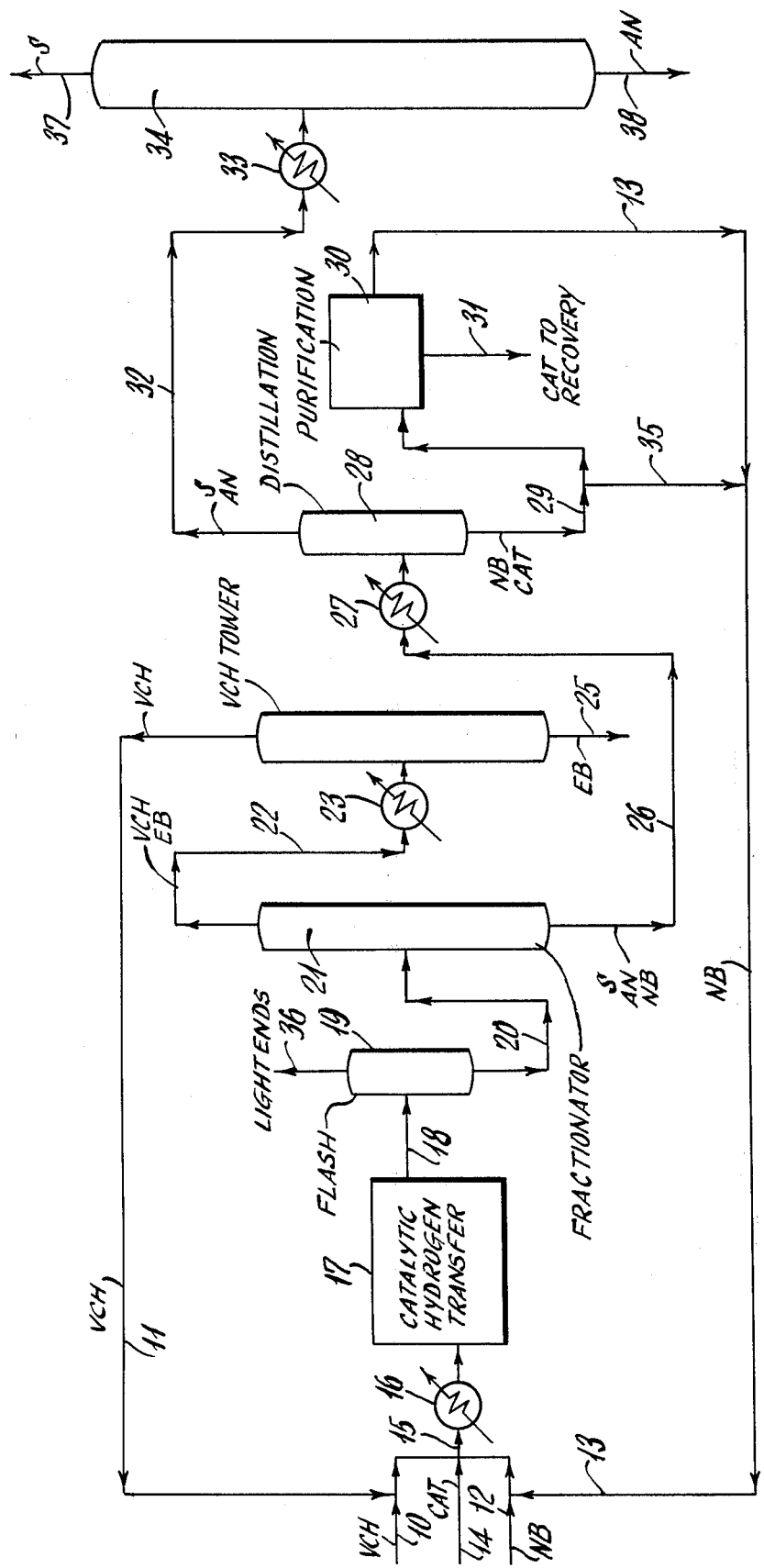

METHOD FOR PREPARING ANILINE BY REACTION OF NITROBENZENE AND VINYLCYCLOHEXENE

This is a continuation, of application Ser. No. 16,674, filed Mar. 1, 1979 which is a divisional of Ser. No. 934,789 filed Aug. 18, 1978 both now abandoned.

FIELD OF THE INVENTION

This invention relates to conversion of hydrocarbons such as 4-vinyl-1 cyclohexene to aromatic products such as ethylbenzene. More particularly it relates to the use of a catalyst to effect such conversions.

BACKGROUND OF THE INVENTION

As is well known to those skilled in the art, it is possible to prepare styrene from ethylbenzene; and there are various processes for providing ethylbenzene charge. A continuing need for increased styrene production may result in increased demand for ethylbenzene. Simultaneously it is found that decreased use of butadiene in rubber compositions results in over-supply of this material; and thus there is a source of raw material which may readily be converted (by well known processes for dimerization) to vinyl cyclohexene.

It is known (Bin Din et al, Synthesis 1978 pages 23–24) that nitro compounds may be reduced to amines in the presence of hot liquid paraffin at 360°–390° C.

SUMMARY OF THE INVENTION

In accordance with certain of its aspects, the novel method of this invention may comprise passing a charge stream containing vinyl cyclohexene and $R'NO_2$, wherein R' is alkyl, cycloalkyl, aryl, aralkyl, or alkaryl, into contact with a hydrogen transfer catalyst at hydrogen transfer conditions thereby forming product stream containing ethylbenzene; and recovering said product stream containing ethylbenzene.

DESCRIPTION OF THE INVENTION

Charge hydrocarbon to the process of this invention is vinyl cyclohexene. 4-vinyl-1-cyclohexene, sometimes referred to as "butadiene dimer," may be commercially available or it may be prepared by dimerization of butadiene by well known processes typified by that set forth at U.S. Pat. No. 2,544,808 to A. E. Staley, or *The Chemistry of Petrochemicals* by M. J. Astle (1956) page 123. Although the process of this invention may be employed to convert 2-vinyl-1-cyclohexene or 3-vinyl-1-cyclohexene to desired products, it is found that the advantages of this process may be more readily attained using, as charge, the 4-vinyl-1-cyclohexene isomer.

The charge vinyl cyclohexene may be used as recovered in impure or crude form or it may be purified. Preferably it will be free of any added stabilizers.

The process of this invention may be carried out by reacting the vinyl cyclohexene with a nitrohydrocarbon $R'NO_2$ wherein R' is a hydrocarbon moiety selected from the group consisting of alkyl, cycloalkyl, alkaryl, aryl and aralkyl.

Although it may be possible to utilize polynitro compounds such as dinitrobenzene etc. and such compounds are included in the representation $R'NO_2$, it is more preferred to use a mononitro compound.

In the above compound, R' may be a hydrocarbon radical selected from the group consisting of alkyl, cycloalkyl, aralkyl, aryl, and alkaryl including such radicals when inertly substituted. When R' is alkyl, it may typically be propyl, butyl, i-butyl, hexyls, octyls, etc. When R' is cycloalkyl, it may typically be cyclohexyl, etc. When R' is aralkyl, it may typically be benzyl, etc. When R' is aryl, it may typically be phenyl, naphthyl, etc. When R' is alkaryl, it may typically be tolyl, xylyl, etc. R' may be inertly substituted i.e. it may bear a non-reactive substituent such as alkyl, aryl, cycloalkyl, ether, halogen, nitro, etc. Typically inertly substituted R' groups may include p-chlorophenyl, 3-chloro-5-methylphenyl, etc. The preferred R groups may be aryl. R' may preferably be phenyl.

Illustrative compounds $R'NO_2$ may include:

TABLE nitrobenzene
dinitrobenzene
p-nitrotoluene
2,4-dinitrotoluene
p-nitrochlorobenzene
1-nitropropane
p-nitroanisole
1-nitro-n-octane
3-nitrophenol
nitrocyclohexane
1,2-dinitroaniline
6-nitroquinoline
4-nitrobenzonitrile
methyl 4-nitrobenzoate The most preferred of these compounds is nitrobenzene.

In practice of the process of this invention, vinyl cyclohexene is reacted with $R'NO_2$, in the presence of a hydrogen transfer catalyst at hydrogen transfer conditions. Hydrogen transfer catalysts are characterized by the ability of the catalyst system to exchange hydrogen between two molecules of different polarity. The preferred catalysts are homogeneous catalysts.

In practice of the process of this invention according to certain of its aspects, vinyl cyclohexene is reacted with nitrohydrocarbon $R'NO_2$ in the presence of catalyst,

wherein a, b and c are integers and a equals 1 or 2, b equals 1 or 2, and c equals 1 or 2, subject to the proviso that a plus b plus c equals 4.

Preferably a is 1 and b is 1 and c is 2:

In these formulae M is a Group VIII noble metal including ruthenium Ru, rhodium Rh, palladium Pd, osmium Os, iridium Ir, or platinum Pt. Platinum and iridium may be preferred: and iridium is most preferred.

X is halogen: typically chlorine, bromine, or iodine. Chlorine is the preferred halogen.

In the above compound, R may be a hydrocarbon radical selected from the group consisting of alkyl, aralkyl, cycloalkyl aryl, and alkaryl, including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, beta-phenylethyl, etc. When R is cycloalkyl, it may typically be cyclohexyl, cycloheptyl, cyclooctyl, 2-methylcycloheptyl, 3-butylcyclohexyl, 3-methylcyclohexyl, etc.

When R is alkaryl, it may typically be tolyl, xylyl, etc. R may be inertly substituted i.e. it may bear a non-reactive substituent such as alkyl, aryl, cycloalkyl, ether, halogen, etc. The preferred R groups may be lower alkyl, i.e. $C_1$-$C_6$ alkyl, groups including eg methyl, ethyl, n-propyl, i-propyl, butyls, amyls, hexyls, etc. R may more preferably be an aryl group, most preferably phenyl.

The catalysts useful in practice of this invention are typified by the preferred catalyst (known as Vaska's compound):

$IrCl(CO)(Ph_3P)_2$

These compounds, which are ligands or complexes, may be prepared by known prior art techniques typified by that set forth eg at Cotton and Wilkinson, *Advanced Inorganic Chemistry* (3 Ed.) J. Wiley (1972) page 1022.

Illustrative catalysts may include:

TABLE $IrBr(CO)(Ph_3P)_2$
$IrI(CO)(Ph_3P)_2$
$IrCl(CO)((p-CH_3C_6H_4)_3P)_2$
$PtCl(CO)((Ph_3P)_2$
$PtBr(CO)(Ph_3P)_2$
$PdI(CO)(Ph_3P)_2$
$PdCl(CO)(Ph_3P)_2$
$PtBr(CO)(Ph_3P)_2$
$RuBr(CO)(Ph_3P)_2$
$RuCl(CO)(Ph_3P)_2$
$RhCl(CO)(Ph_3P)_2$
$IrCL(CO)((p-CH_3O-C_6H_4)_3P)_2$
$Pt(CO)(Ph_3P)_2$
$PdCl_2(CO)(Ph_3P)$
$PtCl(CO)_2(Ph_3P)$

A second, and less preferred category of hydrogen transfer catalysts is that having the formula:

$M'X_n$ wherein M' is rhenium or a Group VIII noble metal such as ruthenium Ru, rhodium Rh, palladium Pd, osmium Os, iridium Ir, or platinum Pt. Preferably M' is rhodium, ruthenium, or palladium. X is halogen, typically chlorine or bromine. n is the valence of M', typically 2-3 for the Group VIII metals and 5 for rhenium. Typical hydrogen transfer catalysts in this category include:

$RhCl_3$
$RuCl_3$
$PdBr_2$
$PdCl_2$
$ReCl_5$

A third illustrative category of hydrogen transfer catalysts includes salts of halo-acids of Group VIII noble metals. Illustrative of such are alkali metal chloroplatinates typified by ammonium chloroplatinate $(NH_4)_2 PdCl_4$ or potassium chloroplatinate $K_2PtCl_6$ or palladium analogues such as $(NH_4)_2 PdCl_6$, etc.

The process of this invention may be carried out batchwise (in an autoclave) or continuously. The hydrogen transfer reaction conditions for continuous reaction may include the following:

TABLE

| Condition | Broad | Preferred | Typical |
|---|---|---|---|
| Temperature °C. | 170-360 | 170-200 | 200 |
| Pressure psig | 0-500 | 0-100 | 50 |
| LHSV | 0.003-6.0 | 0.006-2.0 | 1.5 |
| Mole ratio of R'NO$_2$ to vinyl cyclohexene | 0.1-1.0 | 0.33-0.67 | 0.67 |
| Mole ratio of catalyst to vinyl cyclohexene | 0.001-0.1 | 0.002-0.005 | 0.0026 |

The hydrogen transfer reaction conditions for batch reaction may include:

TABLE

| Condition | Broad | Preferred | Typical |
|---|---|---|---|
| Temperature °C. | 170-360 | 170-200 | 200 |
| Pressure psig | 0-500 | 0-100 | 50 |
| Time of Reaction | 1-20 | 2-15 | 10 |
| Mole ratio of R'NO$_2$ to vinyl cyclohexene | 0.1-1.0 | 0.3-0.7 | 0.67 |
| Mole ratio of vinyl cyclohexene | 0.001-0.1 | 0.002-0.005 | 0.0026 |

The reaction is typically carried out in liquid phase under autogeneous pressure in the presence of the homogeneous catalysts.

During the course of the typical reaction, in liquid phase, hydrogen transfer occurs, the vinyl cyclohexene being dehydrogenated to produce styrene and ethylbenzene; and nitrobenzene being reduced to aniline:

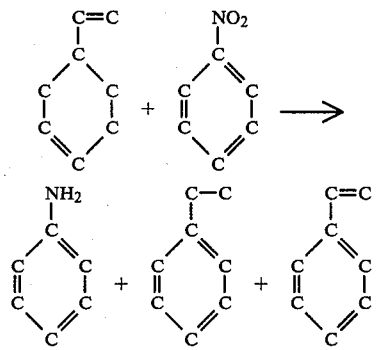

It may be desirable to carry out the reaction in the presence of a diluent-solvent which does not react under the conditions of reaction and such diluent-solvents may include hydrocarbons, preferably aromatic hydrocarbons such as benzene, xylene, toluene, etc., preferably benzene.

Reactor effluent may be characterized (in a preferred embodiment) by the presence of product ethylbenzene (EB), styrene (S), and aniline (AN) and also unreacted charge vinyl cyclohexene (VCH) and nitrobenzene (NB). Typically the yield and selectivities (in mole %) may be as follows:

TABLE

| Selectivity | Broad | Typical |
|---|---|---|
| EB | 10-40 | 30 |
| S | 5-15 | 12 |
| AN | 25-95 | 92 |
| Yield | | |
| EB | 5-25 | 18 |

TABLE-continued

| Selectivity | Broad | Typical |
|---|---|---|
| S | 0-10 | 7 |
| AN | 5-50 | 47 |

It will be clear to those skilled in the art, that the yield and selectivity of a particular product may vary as the catalyst or the particular conditions of ratios, temperatures, pressures, etc. are varied. For example, in batch operation, it is possible to obtain a selectivity at lower temperature of 170°-180° C. for ethylbenzene of ca 30% which is generally about twice as high (ca 15%) of that attained at higher temperature of ca 200° C. Conversely yield and selectivity to aniline are increased to a greater extent by operating at the higher temperature of ca 200° C. Yield of styrene is increased substantially by operating at lower temperature.

In summary, attainment of the desired result is achieved at the following temperature (at the typical operating pressure of ca 40-50 psig):

| Desideratum is Increase in | Preferred Temperature Range °C. |
|---|---|
| EB selectivity | 170-180 |
| EB Yield | 195-205 |
| S Selectivity | 195-205 |
| S Yield | 170-180 |
| AN Selectivity | 200-210 |
| AN Yield | 200-210 |

Reaction effluent from the reaction zone is withdrawn and passed to a fractionation operation. Here there may be obtained several principal product streams:

(i) a small amount of light ends such as ethylene etc. (produced as undesired by-products) which are withdrawn as an overhead eg from a preliminary flashing operation;
(ii) unreacted vinyl cyclohexene which may be recovered and recycled to the reaction zone;
(iii) product:aniline, styrene, and ethylbenzene;
(iv) unreacted nitrobenzene bottoms which (optionally after separation from catalyst) may be recycled to the reaction zone; and
(v) spent catalyst (which optionally may be recycled).

Clearly the particular recovery system will depend upon the composition of the reaction effluent and the preferred product to be recovered.

DESCRIPTION OF PREFERRED EMBODIMENTS

Practice of the novel process of this invention may be apparent from the following description of a preferred embodiment wherein, as elsewhere in this specification, all parts are parts by weight unless otherwise specifically noted. The accompanying drawing represents schematically a flow sheet of one technique whereby the process of this invention may be carried out. It will be apparent to those skilled in the art that the drawing may show major pieces of equipment, and that various pumps, valves, heat exchangers, collection drums, etc. may not be shown.

EXAMPLE I

In this example, there are charged to an autoclave:

16.2 parts (0.15 moles) of 4-vinyl-1-cyclohexene (butadiene dimer)
12.3 parts (0.1 mole) of nitrobenzene
0.3 parts (0.000385 moles) of Vaska's compound
  $IrCl(CO)(Ph_3P)_2$
  chlorocarbonyl bis(triphenylphosphine) iridium The reaction mixture is maintained for 10 hours at 200° C.-202° C./50 psig during which time the charge is converted to produce ethylbenzene, styrene, and aniline. The composition of the reaction mixture is tabulated infra.

EXAMPLE II

In this example, the charge and conditions of Example I were duplicated except that the temperature was 176° C.-178° C.

TABLE

|  | I 200° C.-202° C. | II 176° C.-178° C. |
|---|---|---|
| Selectivity |  |  |
| EB | 16.5 | 28.4 |
| S | 14.1 | 11.6 |
| AN | 91.8 | 28.6 |
| Yield |  |  |
| EB | 10.2 | 18 |
| S | 0.7 | 7.3 |
| AN | 46.5 | 8 |

$$\text{Selectivity} = \frac{\text{Moles product} \times 100}{\text{Moles appropriate starting material consumed}}$$

$$\text{Yield} = \frac{\text{Moles product} \times 100}{\text{Moles appropriate starting material charged}}$$

From illustrative Examples I and II, it will be apparent that:

(i) Higher selectivity and higher yield of ethylbenzene may be achieved at lower temperature of 176° C.-178° C. than are attained at higher temperature of 200° C.-202° C.;
(ii) Higher selectivity and higher yield of aniline may be achieved at higher temperature of 200° C.-202° C. than are attained at lower temperature of 176° C.-178° C.
(iii) Higher selectivity to styrene is attained at higher temperature of 200° C.-202° C.; but higher yield may be achieved at lower temperature of 176° C.-178° C.

Results comparable to those attained in Examples I-II may be attained if the nitrocompound is:

| Example | R'NO$_2$ |
|---|---|
| III | dinitrobenzene |
| IV | p-nitrotoluene |
| V | 2,4-dinitrotoluene |
| VI | p-nitrochlorobenzene |
| VII | 1-nitropropane |
| VIII | nitrocyclohexane |

Comparable results may be attained if the catalyst is:

| Example | Catalyst |
|---|---|
| IX | IrBr(CO) (Ph$_3$P)$_2$ |
| X | PtCl(CO) (Ph$_3$P)$_2$ |
| XI | IrCl(CO)((p-CH$_3$C$_6$H$_4$)$_3$P)$_2$ |
| XII | PdCl (CO) (Ph$_3$P)$_2$ |
| XIII | RhI(CO) (Ph$_3$P)$_2$ |
| XIV | IrCl(CO)((p-CH$_3$O—C$_6$H$_4$)$_3$P)$_2$ |
| XV | RhCl(CO)((p-CH$_3$C$_6$H$_4$)$_3$P)$_2$ |
| XVI | Pt(CO) (Ph$_3$P)$_2$ |
| XVII | PdCl$_2$(CO) (Ph$_3$P)$_2$ |

| Example | Catalyst |
| --- | --- |
| XVIII | PtCl(CO)$_2$(Ph$_3$P)$_2$ |

EXAMPLE XIX

The process of this invention may be carried out continuously in accordance with the schematic flow sheet shown in the drawing.

In this embodiment, there is admitted through line 10 charge 4-vinyl-1-cyclohexene (676.4 parts) which is combined with 143.3 parts of recycle VCH from line 11. Charge nitrobenzene (284.7 parts) is added through line 12 together with 337.9 parts of recycle NB through line 13 to total 662.6 parts total charge NB. There is added through line 14, catalyst (7 parts) Vaska's compound chlorocarbonyl bis(triphenylphosphine) iridium.

Charge containing VCH, NB, and catalyst is passed through line 15 and heated in heat exchanger 16 to ca. 200° C./50 psig. The mixture is passed through reaction zone 17 at LHSV of 1.5. Reaction effluent in line 18 is flashed in flash drum 19 to yield 2.3 parts of light ends withdrawn through line 36. Flashed liquid is passed through line 20 to fractionator 21 from which overhead may be withdrawn containing 143.3 parts VCH and 50.7 parts of EB. This fractionator overhead is passed through line 22 and heat exchanger 23 to VCH tower 24 from which 143.3 parts VCH is recovered and recycled through line 11. Bottoms from VCH tower 24 include 50.7 parts EB recovered through line 25.

Bottoms from fractionator 21 containing styrene, aniline, and nitrobenzene are passed through line 26 and heat exchanger 27 to distillation tower 28 from which there are recovered through line 29 bottoms containing nitrobenzene and catalyst. This stream is passed to purification operation 30 from which catalyst is passed to recovery through line 31 and 337.9 parts of nitrobenzene are recovered through line 13 and recycled to charge. Optionally nitrobenzene plus catalyst may be recycled through line 35 to the charge.

Overhead from distillation tower 28 containing 31.5 parts of styrene and 100 parts of aniline are passed through line 32 and heat exchanger 33 to rectification tower 34. Here 31.5 parts of styrene are recovered as overhead in line 37 and 100 parts of aniline are recovered as bottoms in line 38.

Although this invention has been illustrated by reference to specific embodiments, it will be apparent to those skilled in the art that various changes and modifications may be made which clearly fall within the scope of this invention.

We claim:

1. The method for preparing aniline which comprises passing a charge stream containing vinyl cyclohexene and R'NO$_2$, wherein R' is alkyl, cycloalkyl, aryl, aralkyl, or alkaryl, into contact with homogeneous hydrogen transfer catalyst at hydrogen transfer conditions thereby forming product stream containing aniline; and recovering said product stream containing aniline.

2. The method for preparing aniline of claim 1 wherein said hydrogen transfer conditions include a temperature of 170° C.–360° C. and pressure of 0–500 psig.

3. The method for preparing aniline of claim 1 wherein said hydrogen transfer conditions include a temperature of about 170° C.–200° C.

4. The method for preparing aniline of claim 1 wherein said vinyl cyclohexene is 4-vinyl-1-cyclohexene.

5. The method for preparing aniline of claim 1 wherein said R'NO$_2$ is nitrobenzene.

6. The method for preparing aniline which comprises passing a charge stream containing 4-vinyl-1-cyclohexene and nitrobenzene at 170° C.–360° C. into contact with, as catalyst

wherein M is a Group VIII noble metal, X is halogen, and R is a hydrocarbon moiety selected from the group consisting of alkyl, cycloalkyl, aryl, alkaryl, and aralkyl, thereby forming product stream containing aniline; and recovering said product stream containing aniline.

7. The method for preparing aniline which comprises passing a charge stream containing vinyl cyclohexene and R'NO$_2$ into contact with, as hydrogen transfer catalyst

wherein a, b and c are integers 1–2 and a+b+c is 4, M is a Group VIII noble metal, X is halogen, R is a hydrocarbon moiety selected from the group consisting of alkyl, cycloalkyl, aryl, alkaryl, and aralkyl, and R' is alkyl, cycloalkyl, aralkyl, aryl or alkaryl, thereby forming product stream containing aniline; and recovering said product stream containing aniline.

8. The method for preparing aniline claimed in claim 7 wherein said catalyst is MX(CO)(R$_3$P)$_2$.

9. The method for preparing aniline claimed in claim 7 wherein X is chloride.

10. The method for preparing aniline claimed in claim 7 wherein R is aryl.

11. The method for preparing aniline claimed in claim 7 wherein R is phenyl.

12. The method for preparing aniline claimed in claim 7 wherein R' is aryl.

13. The method for preparing aniline claimed in claim 7 wherein R' is phenyl.

14. The method for preparing aniline claimed in claim 7 wherein said contact is effected at about 170° C.–200° C.

15. The method for preparing aniline which comprises passing a charge stream containing vinyl cyclohexene and nitrobenzene into contact with, as hydrogen transfer catalyst,

thereby forming a product stream containing aniline; and recovering said product stream containing aniline.

16. The method claimed in claim 15 wherein said reaction is carried out at 170° C.–360° C.

17. The method claimed in claim 15 wherein said reaction is carried out at about 170° C.–200° C.

18. The method for preparing aniline which comprises passing charge stream containing vinyl cyclohexene and R'NO$_2$ into contact with, as hydrogen transfer catalyst, M'X$_n$ wherein M' is rhenium or a Group VIII noble metal of valence n, and X is halogen, thereby forming product stream containing aniline; and recovering said product stream containing aniline.

19. The method for preparing aniline claimed in claim 18 wherein said catalyst is a chloride of rhodium, ruthenium, or palladium.

20. The method for preparing aniline claimed in claim 18 wherein said catalyst is rhodium trichloride, RhCl$_3$.

21. The method for preparing aniline claimed in claim 18 wherein said contacting is carried out at about 170° C.–200° C.

22. The method for preparing aniline which comprises passing charge stream containing vinyl cyclohexene and R'NO$_2$ into contact with, as hydrogen transfer catalyst, a salt of a halo acid of a Group VIII noble metal thereby forming product stream containing aniline; and recovering said product stream containing aniline.

23. The method claimed in claim 22 wherein said catalyst is an alkali metal chloroplatinate.

24. The method claimed in claim 22 wherein said catalyst is ammonium chloroplatinate.

25. The method claimed in claim 22 wherein said catalyst is ammonium chloropalladate.

26. The method claimed in claim 22 wherein said contacting is carried out at about 170° C.–200° C.

* * * * *